(12) United States Patent
Redtenbacher et al.

(10) Patent No.: US 6,858,027 B2
(45) Date of Patent: Feb. 22, 2005

(54) VEIN STRIPPING INSTRUMENT

(75) Inventors: Michael Redtenbacher, Vienna (AT); Peter Groll, Vienna (AT); Johann Franke, Vienna (AT)

(73) Assignee: E-Globe Technologies Ltd., Nicosia (CY)

( * ) Notice: Subject to any disclaimer, the term of this patent is extended or adjusted under 35 U.S.C. 154(b) by 0 days.

(21) Appl. No.: 10/161,859

(22) Filed: Jun. 4, 2002

(65) Prior Publication Data

US 2002/0183744 A1 Dec. 5, 2002

Related U.S. Application Data

(60) Provisional application No. 60/295,983, filed on Jun. 5, 2001, provisional application No. 60/358,905, filed on Feb. 20, 2002, and provisional application No. 60/382,767, filed on May 23, 2002.

(30) Foreign Application Priority Data

| Jun. 5, 2001 | (AT) | 874/2001 |
| Feb. 20, 2002 | (AT) | 259/2002 |
| May 23, 2002 | (AT) | 790/2002 |

(51) Int. Cl.$^7$ .............................................. A61B 18/18
(52) U.S. Cl. ........................................................ 606/48
(58) Field of Search ....................................... 606/27–52

(56) References Cited

U.S. PATENT DOCUMENTS

| 5,899,912 A | * | 5/1999 | Eaves, III ................... 606/159 |
| 5,989,249 A | | 11/1999 | Kirwan, Jr. |
| 6,019,771 A | * | 2/2000 | Bennett et al. ............ 606/159 |
| 6,022,313 A | * | 2/2000 | Ginn et al. ................. 600/114 |
| 6,293,944 B1 | | 9/2001 | Ellman et al. |

* cited by examiner

*Primary Examiner*—Roy D. Gibson
*Assistant Examiner*—Pete Vrettakos
(74) *Attorney, Agent, or Firm*—Henry M. Feiereisen

(57) ABSTRACT

A vein stripper, includes a probe, and a coagulation and cutting instrument, which has an electrode assembly and a first end face formed with an opening for passage of the probe. The electrode assembly has at least two electrodes arranged in neighboring disposition in a peripheral zone of the coagulation and cutting instrument in an area of the opening.

25 Claims, 13 Drawing Sheets

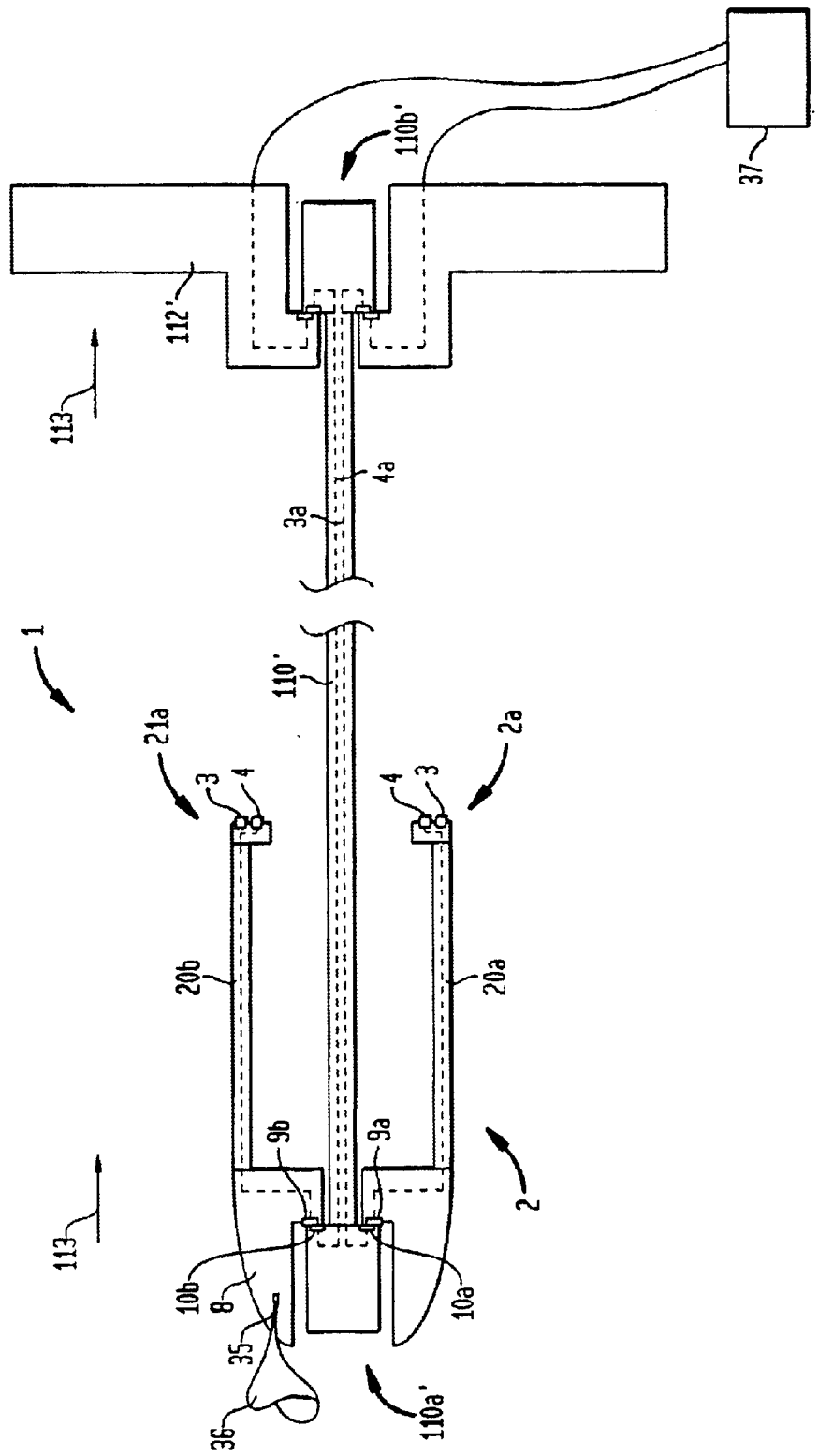

VEIN STRIPPING INSTRUMENT

CROSS-REFERENCES TO RELATED APPLICATIONS

This application claims the benefit of prior filed provisional applications, Application Nos. 60/295,983, filed Jun. 5, 2001, 60/358,905, filed Feb. 20, 2002, and 60/382,767, filed May 23, 2002, pursuant to 35 U.S.C. 119(e), the subject matter of which is incorporated herein by reference.

This application claims the priority of Austrian Patent Applications, Serial Nos. A 874/2001, filed Jun. 5, 2001, A 259/2002, filed Feb. 20, 2002, and A 790/2002, filed May 23, 2002, pursuant to 35 U.S.C. 119(a)–(d), the subject matter of which is incorporated herein by reference.

BACKGROUND OF THE INVENTION

The present invention relates, in general, to a vein stripping instrument, and more particularly to a vein stripper of a type having a probe and a coagulation and cutting instrument which has an opening on one end face for passage of the probe and an electrode.

Vein strippers are used in the surgical field. Russian Pat. No. SU 1,498,473 A1 describes a vein stripper which is connected to a probe. The vein stripper includes a ring knife having an attachment formed with an opening for receiving an electrode. The ring knife is configured as additional electrode. During vein stripping procedure, tissue around the vein is cut by the ring knife. An increased mechanical resistance indicates a capture of venous side branches. Then, through turning the vein extractor, the venous side branch can be severed with the cutting edge of the attachment and coagulated with the electrode by means of high frequency currents. The vein extractor according to SU 1,498,473 A1 has the drawback that smaller venous side branches are cut without noticeable increase in the mechanical resistance and thus not coagulated. A further drawback is the fact that the venous side branches can only be coagulated when recognized shortly before cutting. However, in the event a venous side branch is recognized, but already severed, the required position of the vein extractor for coagulation can no longer be ascertained. This refers to the position in longitudinal direction of the vein extractor as well as to the rotational angle to be adjusted. Coagulation is a fairly complicated process and takes a long time. A further drawback of the vein extractor of SU 1,498,473 A1 is the occurrence of bleeding in the surrounding tissue of the veins as a consequence of the stress during vein stripping, whereby these veins are not coagulated. Furthermore, the sharp cutting edge of the ring knife may lead to inadvertent injuries of surrounding tissue.

It would therefore be desirable and advantageous to provide an improved vein stripper to obviate prior art shortcomings and to ensure coagulation of substantially all venous side branches.

It would also be desirable and advantageous to provide an improved vein stripper which enables coagulation of injured veins in the surrounding tissue, while keeping damage to the surrounding tissue as a result of inadvertent cuts to a minimum, and still allowing cutting and coagulation processes in a single operating step.

It would also be desirable and advantageous to provide an improved vein stripper which enables coagulation of all venous side branches, without adversely affecting surrounding tissue through inadvertent cuts, while ensuring a cutting and coagulation in a single surgical step in a simple and secure manner.

SUMMARY OF THE INVENTION

According to one aspect of the present invention, a vein stripper, includes a probe, and a coagulation and cutting instrument, which has an electrode assembly and a first end face formed with an opening for passage of the probe, wherein the electrode assembly has at least two electrodes arranged in neighboring disposition in a peripheral zone of the coagulation and cutting instrument in an area of the opening.

A vein stripper according to the invention results in a blood-dry strip lumen so that the need for compression bandages is no longer required. Trauma of surrounding tissue is substantially eliminated so that the surgery can be performed with a vein stripper according to the invention year round and is not necessarily limited to the cold season. A further advantage resides in the fact that conventional vein strippers can easily be retrofitted.

According to another aspect of the present invention, a vein stripper, includes a probe, and a coagulation and cutting instrument, which has an electrode assembly and an opening on one end face for passage of the probe, wherein the electrode assembly includes at least one electrode formed by the probe, at least along a portion thereof. This embodiment has the advantage that the spatial separation of the electrodes considerably reduces the risk of short circuit. Also this type of vein stripper realizes a blood-dry strip lumen and thereby eliminates the need for compression bandages, and substantially eliminates any trauma to surrounding tissue so that surgery can be performed year round.

Suitably, the electrode assembly has another electrode formed in the peripheral area of the coagulation and cutting instrument. In this way, coagulation is ensured in all directions around the opening.

According to another feature of the present invention, at least one of the electrodes may be ring-shaped. The ring-shaped configuration of the electrode ensures a surrounding relationship with the opening. It is also conceivable to configure at least one of the electrodes of helical configuration so that the electrode multiply circumscribes the opening.

According to another feature of the present invention, at least one of the electrodes may have gaps. These gaps can be used to guide the other electrodes so as to arrange the electrodes in a plane.

According to another feature of the present invention, at least one of the electrodes may include fan-like fingers to thereby significantly enlarge the area for coagulation and cutting so that the effectiveness of the coagulation of all venous side branches is considerably improved.

According to another feature of the present invention, there may be provided a closure piece or a holding unit arranged on the coagulation and cutting instrument for connection of one end of the probe with the coagulation and cutting instrument. As a result of the connection with the probe, the vein stripper according to the invention can be used in analogous manner as a conventional vein stripper so that the risk of faulty handling can be reduced.

According to another feature of the present invention, the probe may be secured to the coagulation and cutting instrument, thereby substantially eliminating any risk of faulty handling.

According to another feature of the present invention, the coagulation and cutting instrument may include a displacement unit, in particular a handle, and the probe is configured as guide wire. The displacement unit allows a movement of the coagulation and cutting device over the probe so that the probe is not moved conjointly and provides guidance. Thus, the vein can be cut out first and the venous side branches coagulated. Then, the vein can be extracted. In this way, there is no need for the coagulation and culling instrument to capture the vein so that the dimensions of the coagulation and culling instrument can be kept small.

According to another feature of the present invention, the coagulation and cutting instrument may include a drive assembly so as to be self-propelled for movement along the probe. The use of a drive assembly eliminates the need for a displacement unit. Movement of the coagulation and cutting instrument along a curved probe is hereby facilitated.

According to another feature of the present invention, the electrode assembly of the coagulation and cutting instrument may include a further electrode so as to have at least three electrodes. The provision of further electrodes enlarges the area for cutting and/or coagulation, so that the effectiveness of coagulation of all venous side branches is enhanced. Suitably, the further electrode may be arranged on a wall surface of the coagulation and cutting instrument. Attachment of the further electrode to the wall surface of the coagulation and cutting instrument increases the coagulation zone after severing a venous side branch, so that the effectiveness of coagulation of all venous side branches is enhanced.

According to another feature of the present invention, the electrodes can be spaced from one another at different distances. The selection of different distances realizes different activation zones between two electrodes.

According to another feature of the present invention, at least one of the electrodes may be connected to a resistor, so that varying activation zones can be realized.

According to another feature of the present invention, the coagulation and cutting instrument may have a base body defining a longitudinal axis and forming the first end face for arrangement of the at least two electrodes. The attachment of the electrodes to the first end face ensures that venous side branches reach the activation zone of the electrodes before they would tear off. The at least two electrodes of the coagulation and cutting instrument may have a ring-shaped configuration and define symmetry axes in substantial parallel relationship to one another, wherein the ring-shaped electrodes define areas which substantially overlap in an axial direction of the symmetry axes. This configuration of the coagulation and cutting instrument is simple in structure and does not require a configuration of the probe as electrode.

According to another feature of the present invention, the electrode assembly may include a further ring-shaped electrode which is defined by a symmetry axis in substantial parallel relationship to the symmetry axes of the at least two other electrodes, and which describes an area, whereby the area of the further electrode and the areas of the at least two electrodes substantially overlap, as viewed in axial direction of the symmetry axes. The provision of at least three ring-shaped electrodes improves the effectiveness of the coagulation of all venous side branches. Suitably, the symmetry axes of the ring-shaped electrodes may extend in substantial parallel relationship to the longitudinal axis of the base body. This configuration realizes a rotation-symmetrical action by the electrodes so that an inadvertent turning of the coagulation and cutting instrument does not result in a decreased effectiveness. The ring-shaped electrodes may also extend in a same plane, which is oriented substantially normal to the longitudinal axis of the base body. This configuration improves in particular the cutting action of the coagulation and cutting instrument and requires only a very small pulling force to effect the coagulation and cutting procedure.

According to another feature of the present invention, the base body may demarcate a substantially cylindrical space. In this way, the coagulation and cutting instrument can be closely arranged about the vein, and moreover, the second end face of the base body can be attached to a closure piece of a conventional vein stripper and conjointly pulled over the vein so that venous side branches can be severed by the coagulation and cutting instrument.

According to another feature of the present invention, the base body may include at least one shaft aligned in the longitudinal axis of the base body. The provision of a shaft allows a sufficient expansion of the vein, when the vein arches as the base body of the coagulation and cutting instrument is pulled therethrough, so that a clogging of the base body is precluded and the coagulation and cutting instrument can be designed of small length.

According to another feature of the present invention, the base body may be provided in the area of the second end face with the holding unit for receiving and securing the end of the probe. The need for a separate closure piece of the vein stripper is hereby eliminated. Furthermore, a use of the coagulation and cutting instrument in incorrect direction is precluded so that the risk of faulty handling is reduced.

According to another feature of the present invention, the holding unit may be secured to the second end face of the base body. The attachment of the holding unit on the second end face reduces the structural length of the coagulation and cutting instrument.

According to another feature of the present invention, the holding unit provides a form-fitting connection between the one end of the probe and the base body. The form-fitting configuration of the connection prevents an inadvertent loosening thereof.

According to another feature of the present invention, the holding unit may be realized by a slit formed in a sidewall of the base body for receiving the probe and a pocket for receiving the end of the probe, wherein the pocket has a side which confronts the first end face of the base body and includes a web to narrow this side. This configuration enables a simple and secure connection between the probe and the base body. Suitably, the pocket may have a prolongation on this side. The provision of the prolongation improves the durability of the connection.

According to another feature of the present invention, there may be provided electric lines for connecting the electrodes with an electric power supply source, wherein the electric lines are guided outwards from the base body at a central location of the second end face of the base body. In this way, the coagulation and cutting instrument can be moved by means of the electrical lines without any tilting moment.

According to another feature of the present invention, the holding unit may have two contacts which are conductively connected with the electrodes, and the electric lines for connecting the electrodes with the electric power supply source are guided within the probe and connected with further contacts at the end of the probe, whereby the electrically conductive connection between the ring-shaped electrodes and the electric power supply source is realized by the contacts of the holding unit and the contacts at the end of the probe, when the probe is received and secured in the holding unit.

According to another feature of the present invention, there may be provided a drainage tube arranged at the coagulation and cutting instrument. In this way, the drainage tube may be inserted in a single operating step with the stripping in the strip lumen. Suitably, the coagulation and cutting instrument has a second end face opposite to the first end face for arrangement of a fastening assembly for the drainage tube. When using a vein stripper according to the invention for two vein sections, the drainage tube, located in the strip lumen after the first vein piece, can be severed and a further drainage tube can be attached to the coagulation and cutting Instrument.

According to another feature of the present invention, there may be provided a longitudinal slitting structure for slitting a vein in longitudinal direction. The provision of the longitudinal slitting structure allows a guidance of the vein stripper according to the invention around the vein, whereby the vein can be removed from the strip lumen after the vein stripping procedure. This is advantageous because the vein can be maintained in stretched disposition during the stripping procedure. The longitudinal slitting structure may be implemented by a slit electrode for monopolar cutting, a slit electrode for bipolar cutting, or a mechanical blade. Each one of these embodiments ensures a secure slitting of the vein in longitudinal direction. Suitably, the longitudinal slitting structure may be connected to the coagulation and cutting instrument, whereby, optionally, the slit electrode can be connected to the electric lines or a further electric line.

The longitudinal slitting structure may be constructed for locked engagement with the probe, in particular with a groove of the probe. A secure slitting of the vein in longitudinal direction is hereby ensured.

According to another feature of the present invention, the longitudinal slitting structure may be secured in the holding unit, and a further holding unit may be provided for receiving and securing the one end of the probe. This configuration allows a modular construction of the coagulation and cutting instrument and of the longitudinal slitting structure.

According to another feature of the present invention, the coagulation and cutting instrument may be provided in an area of at least one of the electrodes with at least one outlet opening for exit of an ionizable gas, in particular argon. The provision of ionizable gas results in a coagulation already anteriorly of the electrodes so that the risk that incrustation or the like, adhering to one of the electrodes and torn off during movement of the vein stripper, is reduced. The ionizable gas is supplied via a gas line. Suitably, the outlet opening may be connected to a gas supply on the second end face of the base body. The gas supply and the electric lines may hereby be guided in parallel relationship and, optionally, received in a common tube.

According to another feature of the present invention, the coagulation and cutting instrument may have at least one suction opening, so that smoke generated during coagulation can be sucked off and discharged via a suction line. Suitably, the suction opening is arranged in the holding unit so that the suction opening can be configured independently from the coagulation and cutting instrument, while still ensuring a sufficient removal of smoke by suction. The suction opening may be connected to a suction port on the second end face of the base body. In this way, the electric lines, the suction line, and, optionally, the gas supply can be guided in parallel relationship, and, optionally, arranged in a common tube.

According to another feature of the present invention, there may be provided a ring-shaped ultrasonic resonator arranged in the area of the electrodes. The ultrasonic resonator may be configured as cutting instrument and the electrodes as coagulation instrument so that the cutting operation and the coagulation operation can be carried out separately, adjusted and controlled in a simple manner independently from one another.

BRIEF DESCRIPTION OF THE DRAWING

Other features and advantages of the present invention will be more readily apparent upon reading the following description of currently preferred exemplified embodiments of the invention with reference to the accompanying drawing, in which:

FIG. 4F is a sectional view of a fourth embodiment of a vein stripper according to the present invention, having a coagulation and cutting instrument with a holding device provided with contacts, and a probe having incorporated therein electric lines, and a grip provided with contacts;

DETAILED DESCRIPTION OF PREFERRED EMBODIMENTS

Figure 1A:
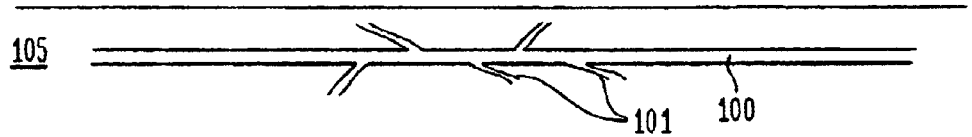
FIG. 1A is a schematic sectional view of a vein with side branches in the connective tissue.

Throughout all the Figures, same or corresponding elements are generally indicated by same reference numerals.

The present invention relates to techniques in the field of electrosurgery or high frequency surgery, and is a directed, in particular, to a procedure involving the coagulation and cutting of biological material or tissue by means of high frequency current flowing through the tissue. The impact on the biological material at low frequency currents involves the electrolytic effect and the Faraday effect. Both these effects are, however, undesired in electrosurgery because they can lead, on the one hand, to electrolytic damages, and, on the other hand, to involuntary muscle contractions. Therefore, only high frequency currents are used in electrosurgery utilizes with frequencies starting at about 300 kHz. At these frequencies, no ion shift in the tissue is encountered and muscle contractions no longer occur. Heating of the tissue is realized through the thermal effect which can be exploited for coagulation or cutting of the tissue.

Coagulation involves a heating of the tissue to about 100° C., whereby intracellular and extracellular liquid evaporates. Tissue shrinks hereby while the cell membranes remain intact. In this way, bleeding can be stopped with great success. During cutting, the tissue is instantly heated to temperatures that are slightly above 100° C., so that the cell membranes are torn apart in an explosion-like fashion. This allows execution of precise incisions in the tissue.

Depending on the configuration of the electrodes for connection to the high frequency power supply source, essentially two techniques of electrosurgery have evolved. In the monopolar technique, a large-area, so-called neutral electrode is attached to the patient's body. The size of the electrode causes only slight current density in this area so that heating is small and negligible. The actual heating action is generated in the area of the active electrode which has a pointed configuration and causes in this area substantial current densities in the tissue. In the bipolar technique, both electrodes are positioned in close proximity next to one another and are integrated in an instrument, if possible. Current flows hereby only in the narrowly defined tissue zone between both electrodes.

The present invention is directed to a vein stripper of the bipolar technique for coagulation and/or cutting of organic material.

Figure 1B:
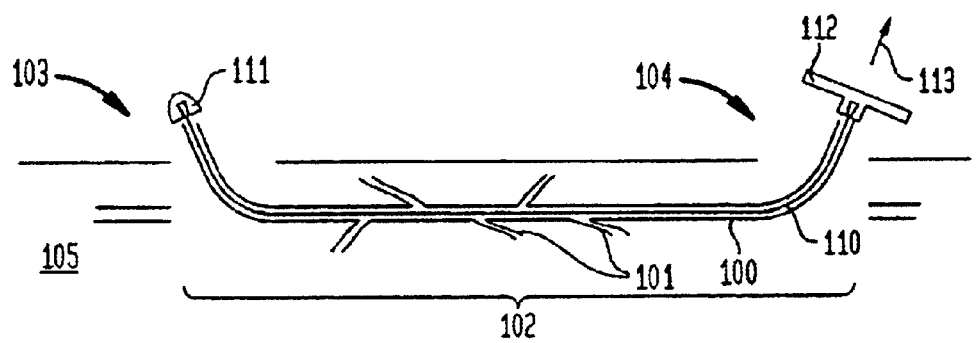
FIG. 1B is a schematic sectional view of the exposed vein of FIG. 1A, showing a probe extending therethrough and having a closing structure on one end and a grip on the other end.
Figure 1C:
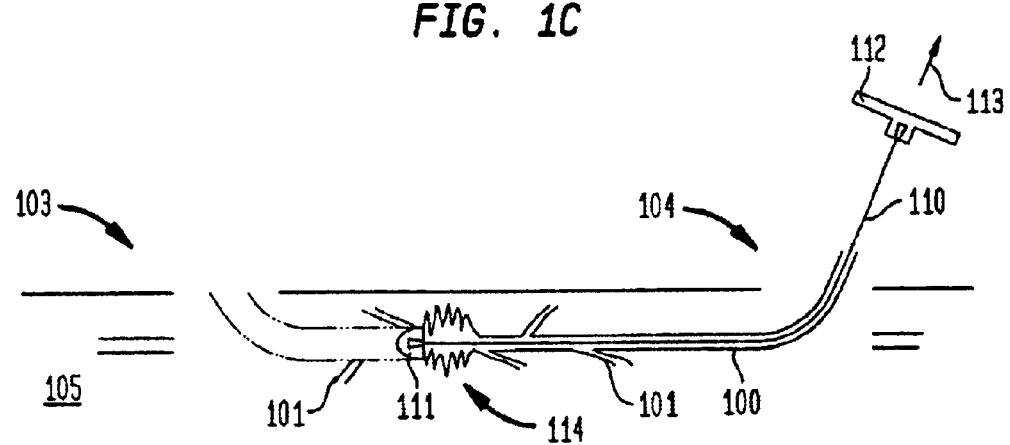
FIG. 1C is a schematic sectional view of the vein of FIG. 1A, showing the formation of widened vein regions during stripping procedure.

Turning now to the drawing, and in particular to FIG. 1, there is shown a schematic sectional view of a vein 100 with side branches 101 in the connective tissue 105. When vessels or veins are diseased, it is often necessary to remove a certain section 102 (FIG. 1B) of the vein 100. Hereby, as shown in FIG. 1B, an incision is made in the connective tissue 105 at the section 102 adjacent to the upper, i.e. heart-proximal area 103 and to the lower, i.e. heart-distal area 104. The vein 100 is then severed, and both ends of the vein section 102 to be extracted are exposed. Next, a probe 110 of a vein stripper is inserted into the vein section 102. A closure piece 111 is attached in the heart-proximal area 103 to the probe 110 to prevent the vein 100 from slipping off the probe 110. Subsequently the probe 110 is pulled by means of a grip 112, provided at the heart-distal area 104, through the connective tissue 105, whereby the vein section 102 is conjointly moved and withdrawn in the heart-distal area 104 in the pulling direction indicated by arrow 113. As shown in FIG. 1C, the region 114 of the vein 100, positioned anteriorly of the closure piece 111 in pulling direction 113, expands, resulting in a distinct fold formation of the vein wall. This procedure has shortcomings because the venous side branches 101, which connect into the vein 100, are ripped off during the extraction process, resulting in substantial bleeding which requires lengthy hospital stays and respective bandaging and immobilization of the treated body part.

This drawback can be eliminated by using a vein stripper according to the invention, which is so constructed that venous side branches 101 are not ripped out together with the vein 100 from the connective tissue 105 or during extraction of the vein section 102, but are sealed beforehand by the inventive and novel vein stripper and then separated from the vein 100. This is realized by electrosurgical coagulation or cutting of the venous side branches 101 in the area of their connection into the vein 100.

Figure 2A:
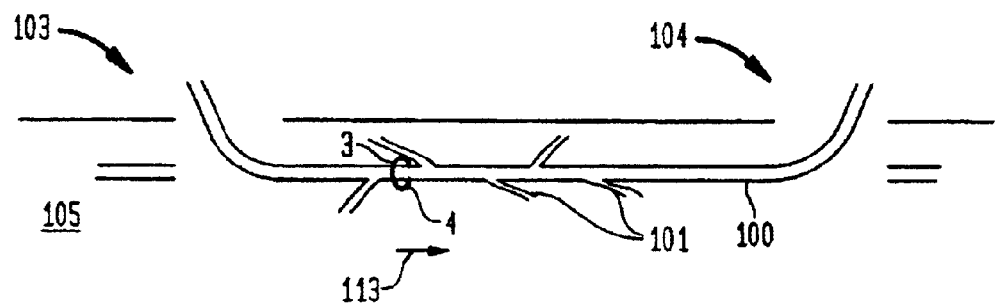
FIG. 2A is a schematic sectional view of a vein in the connective tissue, showing electrodes placed over the vein.
Figure 2B:
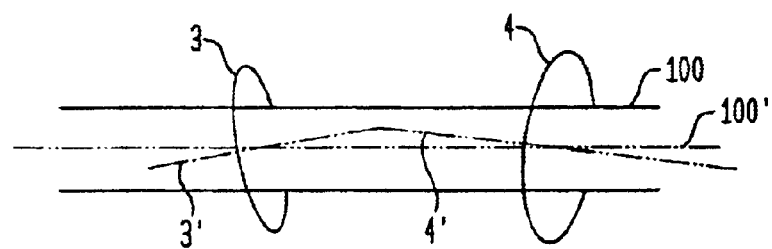
FIG. 2B is a schematic illustration of an arrangement of the electrodes in relation to the vein.
Figure 5A:
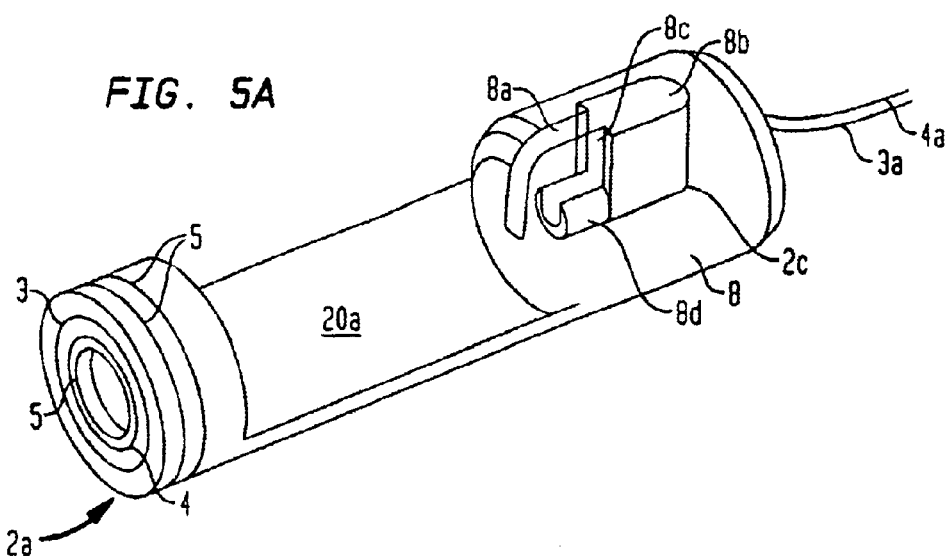
FIG. 5A is a partial sectional view of a ninth embodiment of a vein stripper according to the present invention, having a modified coagulation and cutting unit.
Figure 5B:
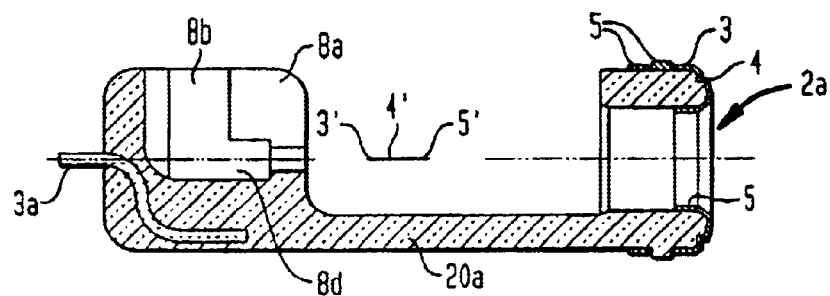
FIG. 5B is a side view of the coagulation and cutting unit according to FIG. 5A.
Figure 5C:
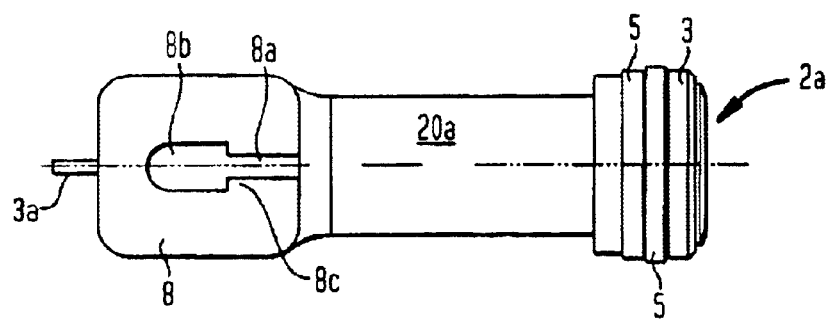
FIG. 5C is a top plan view of the coagulation and cutting unit according to FIG. 5A.
Figure 5D:
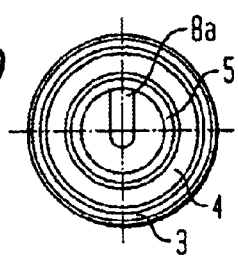
FIG. 5D is a front view of the coagulation and cutting unit according to FIG. 5A.

A vein stripper according to the present invention includes a coagulation and cutting instrument 1 which may have at least two electrodes 3, 4, as shown, e.g., in FIG. 2B of substantially ring-shaped configuration. FIG. 5A shows a variation with three ring shaped electrodes 3, 4, 5. According to another embodiment of a vein stripper according to the present invention, the probe 110 may be configured to represent one of the electrodes, and the coagulation and cutting instrument 1 may be configured with at least one electrode, whereby the vein stripper has again at least two electrodes. In view of their ring shaped configuration, the electrodes 3, 4, 5 can be placed over the vein 100. As a consequence, a generally ring-shaped vein-demarcating region, called activation zone 6 in the following description, is established in which biological material surrounding the vein 100 can be coagulated and cut. Thus, venous side branches 101 in the area of their connection into the vein 100 can be separated from the vein 100, as shown in FIG. 2A. It is hereby possible, on the one hand, to directly sever the venous side branches 101. On the other hand, it is also sufficient to provide a coagulation of the venous side branches 101, which are hereby sealed and cleanly separated at the coagulation site during subsequent withdrawal of the vein section 102, without experiencing any significant bleeding.

The optimum radius of the electrodes 3, 4, 5 is dependent on physiological conditions which are governed by the diameter of the vein 100. Another consideration is, however, to keep the diameter of the electrodes 3, 4, 5 as small as possible so as to limit damage to surrounding connective tissue 105 to a minimum. A ring-shaped configuration of the electrodes 3, 4, 5 is hereby especially advantageous during vein stripping procedure because the electrodes 3, 4, 5 can be placed in particularly close proximity to the vein 100. Of course, other configurations of the electrodes 3, 4, 5 are conceivable, for example, as closed loops with rectangular base. Also these types of electrodes should be considered as substantially ring-shaped within the scope of the present invention.

Placement of the substantially ring-shaped electrodes 3, 4, 5 over the vein 100 is implemented by arranging the electrodes 3, 4, 5 in such a manner that their symmetry axes 3', 4', 5' extend in substantial parallel relationship to the center line 100' of the vein 100 (FIG. 2B). The symmetry axes 3', 4', 5' of the electrodes 3, 4, 5 extend thus substantially parallel to one another. Furthermore, the areas, respectively described by the electrodes 3, 4, 5, overlap, when viewed in axis direction of the symmetry axes 3', 4', 5'. This overlap may be complete or also only partially, depending on the configuration of the individual electrodes 3, 4, 5. Of course, this holds also true for electrodes which do not have a precisely defined symmetry axis, i.e. configurations that have, for example, bulging areas or the like. The arrangement of the substantially ring-shaped electrodes 3, 4, 5 can be implemented in any case in accordance with the arrangement shown in FIG. 2B.

The particular arrangement of the electrodes 3, 4, 5 influences the position and dimension of the activation zone 6, i.e. the area in which the thermal effect upon the tissue is at a maximum. The activation zone 6 is defined by the area in which the current density between the electrodes 3, 4, 5 is at a maximum. Of course, form and structure of the activation zone 6 are dependent also on other factors, in particular the used current strength and voltage. By selecting the input voltage, different methods of coagulation, such as soft coagulation, forced coagulation, and spraying coagulation, can be established.

Turning now to FIGS. 3A to 3D, they are shown various arrangements of the electrodes 3, 4 as well as the activation zones 6 resulting from these arrangements, whereby the activation zones 6 are respectively indicated by dotted lines which are obtained as intersecting lines between the boundary surface of the three-dimensional, substantially ring-shaped activation zone 6 and the drawing plane, which is indicated by the plane 6'. In any event, the activation zone 6, defined by the ring-shaped electrodes 3, 4, is a three-dimensional, substantially ring-shaped area. In general, the activation zone 6 can be defined as torus with circular or also elliptic or rectangular base.

Figure 3A:
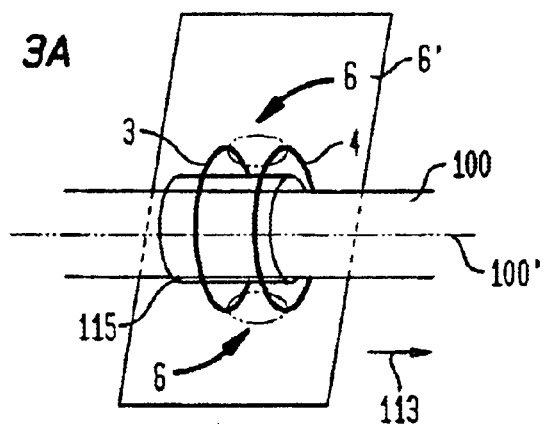
FIG. 3A is a side elevation of an arrangement of the electrodes in two different planes.

FIG. 3A shows an arrangement with two electrodes 3, 4 positioned in different planes in substantially parallel spaced apart relationship. As a result, the activation zone 6 for bipolar coagulation or cutting is positioned between both electrodes 3, 4. As the electrodes 3, 4 are moved in pulling direction 113, a venous side branch 101 is initially captured by the electrode 4. Upon further pulling, the side branch 101 is bent in the activation zone 6, coagulated, and cut. In this case, it is suitable, to provide a separate protective envelope 115 to prevent the vein 100 itself from being severed.

Figure 3B:
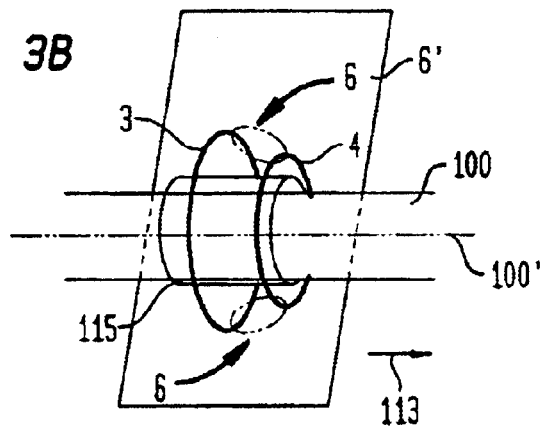
FIG. 3B is a side elevation of another arrangement of the electrodes in two different planes.

FIG. 3B shows an arrangement with two electrodes 3, 4 of different diameter and positioned in different spaced apart planes. In this embodiment, the indicated activation zone 6 causes earlier, i.e. at slighter pull, a cutting or coagulation of the venous side branches 101. Also in this embodiment, the provision of a protective envelope 115 may be suitable.

Figure 3C:
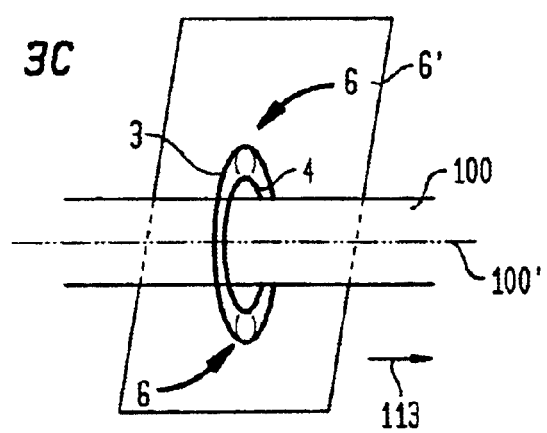
FIG. 3C is a side elevation of still another arrangement of the electrodes in a same plane.

In the arrangement shown in FIG. 3C, the electrodes 3, 4 are positioned in a same plane. As a consequence, the activation zone 6 does not extend substantially beyond the edge defined by the inner electrode 4 and the outer electrodes 3. Thus, the vein 100 does not lie in the activation zone 6. Upon a movement in pulling direction 113, the venous side branches 101 are severed before and in particular during contact with one of both electrodes 3, 4. This facilitates cutting in forward direction because the activation zone 6 lies in pulling direction 113. The provision of a protective envelope 115 is hereby not necessary because a suitable mounting of both electrodes 3, 4 can ensure that the inner electrode 4 is prevented from being positioned too closely to the vein 100.

Of course, other arrangements of the electrodes 3, 4 are possible as well. As shown, for example, in FIG. 3D, the activation zone 6 is limited to an area in which the two electrodes 3, 4 approach closest one another. This embodiment is advantageous, for example for very selective instruments that allow a surgeon to precisely ascertain the coagulation site through turning of the coagulation and cutting instrument 1. Other arrangements may include in addition to the two electrodes 3, 4 further electrodes 5 to thereby alter, especially enlarge the coagulation zone.

An elongated base body 2 may support the electrodes 3, 4, 5 of the coagulation and cutting instrument 1 according to the invention.

FIGS. 4A to 4K show illustrations of various embodiments of a vein stripper according to the invention. Hereby, the electrodes 3, 4 may be attached to an end face 2a of a base body 2 such that the symmetry axes 3', 4' of the electrodes 3, 4 extend in substantial parallel relationship to the longitudinal axis 2' of the base body 2. This arrangement ensures that the electrodes 3, 4, are aligned with respect to the vein 100 in the afore-described manner (especially FIGS. 3A–3D), when the base body 2 is moved in the manner shown, i.e. in pulling direction 113, along the vein 100 and its center line 100'.

Figure 3D:
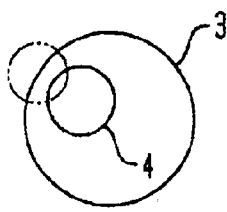
FIG. 3D is a vertical projection of yet another arrangement of the electrodes.
Figure 4A:
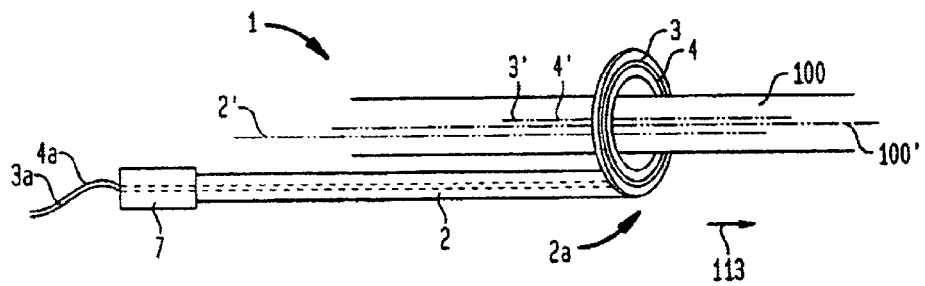
FIG. 4A is a side elevation of a coagulation and cutting unit of a vein stripper according to the present invention.

The base body 2 shown in FIG. 4A is configured in the shape of a shaft having a grip 7 on one end face. Analogous to the embodiment shown in FIG. 3C, the electrodes 3, 4 are positioned at the other end face 2a in one plane, which extends in substantially normal relationship to the longitudinal axis 2' of the base body 2. Of course, configurations of the electrodes 3, 4 according to FIGS. 3A, 3B, 3D are possible as well. Electric lines 3a, 4a connect the electrodes 3, 4 to an electric power supply source 37 (shown, e.g., in FIG. 4F).

Figure 4B:
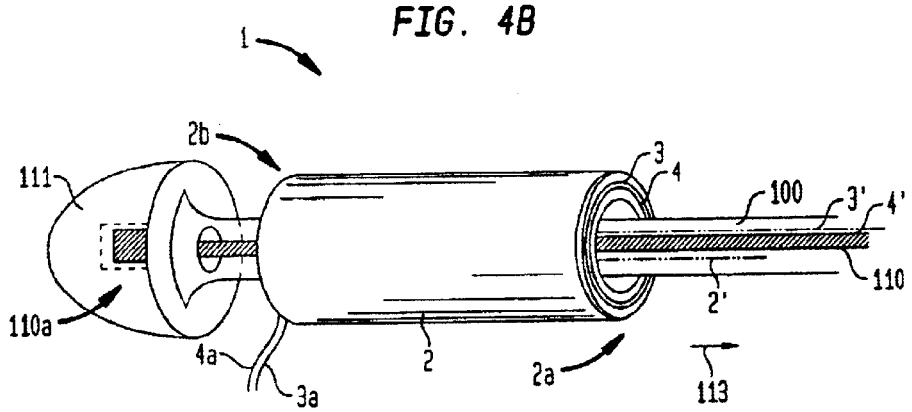
FIG. 4B is a side elevation of a first embodiment of a vein stripper according to the present invention having a coagulation and cutting unit of cylindrical configuration.

The base body 2 shown in FIG. 4B has a substantially cylindrical configuration, whereby the ring-shaped electrodes 3, 4 are attached to the end face 2a of the base body 2 and connected by electric lines 3a, 4a to the electric power supply source 37. Also in this embodiment, the symmetry axes 3', 4' of the electrodes 3, 4 extend in substantial parallel relationship to the longitudinal axis 2' of the base body 2. The cylindrical configuration of the base body 2 allows a placement of the coagulation and cutting instrument 1 over the vein 100, and a guidance of the coagulation and cutting instrument 1 along the vein 100. At the opposite end face 2b, the base body 2 is so designed as to allow attachment of a common closure piece 111 of a vein stripper.

The vein stripping procedure is hereby as follows: After placement of the coagulation and cutting instrument 1 according to the invention onto the exposed end of the vein section 102 to be removed in the area 103 (FIG. 1B) and insertion of the probe 110 into the vein 100, the closure piece 111 can be attached in a known manner onto the probe 110, and the vein 100 can be pulled out in pulling direction 113. This procedure differs from conventional methods by the fact that the coagulation and cutting instrument 1 according to the invention severs and coagulates all venous side branches 101 before these side branches 101 can be ripped off as has been encountered in conjunction with conventional methods.

Of course, conventional vein strippers can easily be retrofitted with a coagulation and cutting instrument 1 according to the present invention.

Figure 4C:
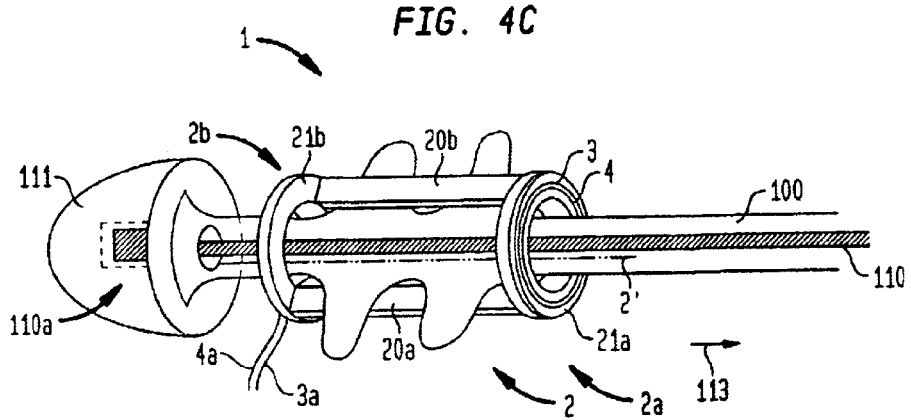
FIG. 4C is a side elevation of a second embodiment of a vein stripper according to the present invention, having a coagulation and cutting unit with two shafts.

FIG. 4C shows a further embodiment of a coagulation and cutting instrument 1 in which the base body 2 includes only two shafts 20a, 20b extending between end rings 21a, 21b. Suitably, the electric lines 3a, 4a, are guided via the shafts 20a, 20b. Of course, while the provision of two shafts 20a, 20b is a currently preferred embodiment, is certainly possible to provide the base body 2 with only one shaft 20a. This configuration of the base body 2, as shown in FIG. 4C, defines a substantially cylindrical envelope which is almost entirely transparent as opposed to the embodiment shown in FIG. 3b. This is advantageous during vein stripping, especially in conjunction with the afore-mentioned fold formation in the vein wall. Withdrawal of the vein 100 from the connective tissue 105 results normally in an expansion of the vein 100 in the region 114 located anteriorly of the closure piece 111 in the pulling direction 113. The embodiment of the coagulation and cutting instrument 1, as shown in FIG. 4C, enables the vein 100 to sufficiently expand over the cylindrical space that is bounded by the base body 2. Compared to a configuration with a closed cylinder, this configuration results in a much shorter base body 2, without experiencing a clogging of the base body 2 as a result of the expansion of the vein 100. Also this configuration is applicable for common vein strippers.

Of course, configurations are also possible which constructively lie between the embodiments shown in FIGS. 4B and 4C. For example, it is possible to provide suitably sized recesses in the outer cylindrical surface area of the base body 2. In this way, the coagulation and cutting instrument can be optimized as far as length and stiffness are concerned. The use of the coagulation and cutting instrument 1 for vein stripping requires only that the spreading out of the vein 100 in the area 114 does not extend in front of the electrodes 3, 4 as viewed in pulling direction 113. If that were the case, venous side branches could no longer be safely coagulated or cut.

Figure 4D:
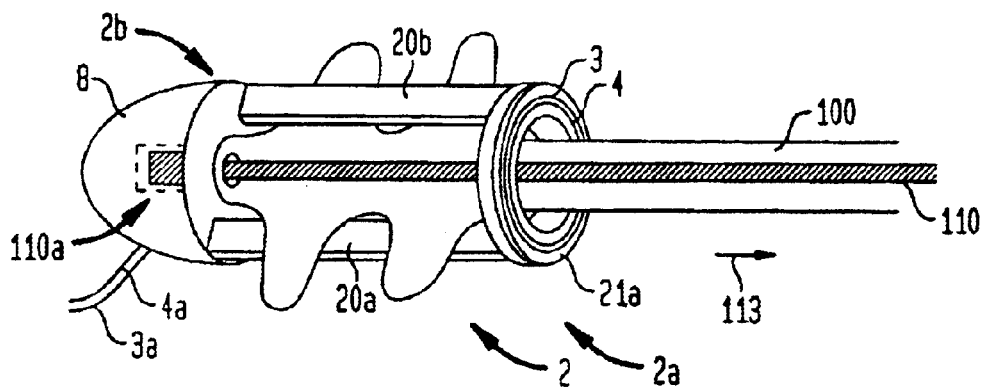
FIG. 4D is a side elevation of a third embodiment of a vein stripper according to the present invention, having a coagulation and cutting instrument with two shafts and a holding device.

In the embodiment of FIG. 4D, a holding device 8 is attached to the end face 2b of the base body 2 for receiving and securement of end 110a of probe 110. Thus, the closure piece 111 is integrated into the base body 2 in this embodiment, thereby further simplifying handling because it is no longer required to attach a separate closure piece. After threading the probe 110 through the exposed vein 100, it is only necessary to place the coagulation and cutting instrument 1 according to the invention over the vein 100 and to secure the end 110a of the probe 110 upon the base body 2 or holding device 8. Hereby, the holding device 8 is suitably configured in a similar manner as conventional closure pieces of conventional vein strippers.

Figure 4E:
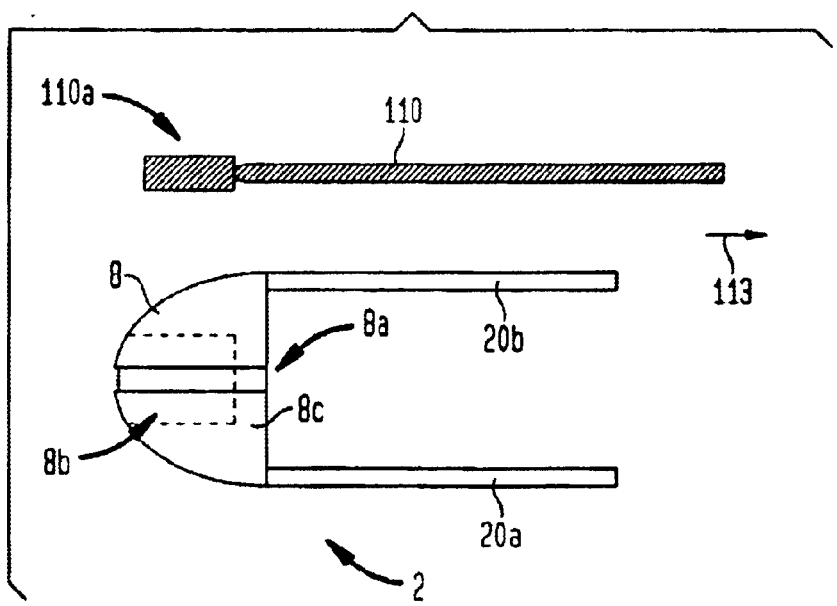
FIG. 4E is a sectional view of the holding device of the coagulation and cutting instrument and the probe according to FIG. 4D.

As shown in particular in FIG. 4E, the holding device 8 is formed with a slot 8a for passage of the probe 110, and pocket 8b for receiving the end 110a of the probe 110, and is further formed with a shoulder 8c for preventing the probe end 110a from slipping out. This embodiment facilitates manipulations during vein stripping procedure and in particular prevents the base body 2 from being placed over the vein 100 in an incorrect direction.

In the embodiment of FIG. 4F, the connection of the electrodes 3, 4 to the power supply source 37 is implemented via probe 110'. Therefore, there is no need for a separate cable that has to be guided through the vein 100 before vein stripping procedure or has to be pulled along during extraction of the vein 100 through the connective tissue 105. The holding device 8 of the coagulation and cutting instrument 1 includes two contacts 9a, 9b, which are connected in an electrically conductive manner with the electrodes 3, 4, and a particular probe 110', which has fused therein two electric lines 3a, 4a. The probe 110' has one end 110a' formed with two contacts 10a, 10b. After threading the probe 110' through the vein 100, the coagulation and cutting instrument 1 is connected with the end 110a' of the probe 110' in a same manner as the coagulation and cutting instrument 1 of FIG. 4D. Hereby, a contact is established between the contacts 9a, 9b and 10a, 10b to thereby connect the ring-shaped electrodes 3, 4 via the probe 110' with the power supply.

Preferably, the probe 110' is provided on both ends 110a', 110b' with electrodes 10a, 10b and further includes a separate grip 112' which provides in analogous manner an electric connection to the electric lines 3a, 4a. The grip 112' has hereby also electrodes which are connected to electric lines leading to the power supply. The embodiment of the vein stripper of FIG. 4F allows a particularly simple vein stripping procedure. After threading the probe 110' through the vein 100 and after placement of the coagulation and cutting instrument 1 to one end 11a' of the probe 110' and attachment of the grip 112, which is the connected to the power supply, to the other end 110b', the electrodes 3, 4 are connected via the grip 112' and the probe 110' with the powered supply. As a result, the vein 100 can be extracted, whereby all venous side branches 101 are ensured to be severed by the electrodes 3. 4.

Figure 4G:
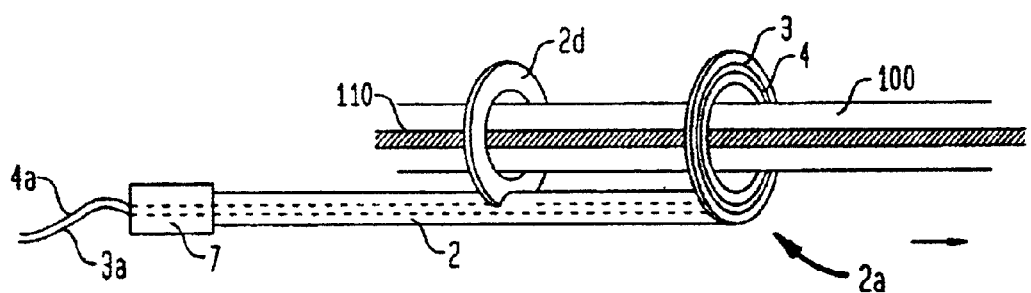
FIG. 4G is a sectional view of a fifth embodiment of a vein stripper according to the present invention, having a coagulation and cutting instrument with a displacement device.

FIG. 4G shows a vein stripper according to the invention in correspondence to the embodiment of FIG. 4A, whereby the probe 110 is inserted into the vein 100 prior to the stripping procedure for guiding the coagulation and cutting instrument 1. This prevents a severing of the vein 100 so that the vein stripper according to FIG. 4G also includes a probe. Guidance of the coagulation and cutting instrument 1 is realized by the presence of a guide ring 2d to thereby ensure that the coagulation and cutting instrument 1 is guided around the vein.

Figure 4H:
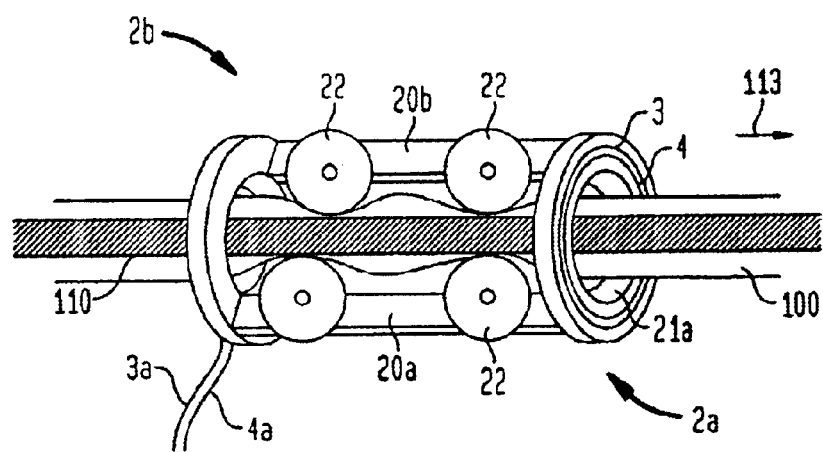
FIG. 4H is a sectional view of a fifth embodiment of a vein stripper according to the present invention, having a coagulation and cutting instrument with a drive assembly.

FIG. 4H shows a vein stripper according to the invention, including a drive assembly 22 which includes wheels 22 and is provided to move the coagulation and cutting instrument 1 along the probe 110 to thereby separate the vein 100 from the connective tissue 105 and the venous side branches 101. No additional push and/or pull devices are required in this embodiment.

The vein stripper according to FIGS. 4G and 4H have the advantage that the vein 100 can be separated in a first operating step from the connective tissue 105 and the venous side branches 101, and that the vein 100 is extracted only in a second operating step. As a consequence, there is no need to provide the coagulation and cutting instrument 1 with regions for receiving already stripped vein 100 as the vein 100 remains unchanged in the body so that small structures can be realized for implementing the vein stripper according to the invention.

Figure 4I:
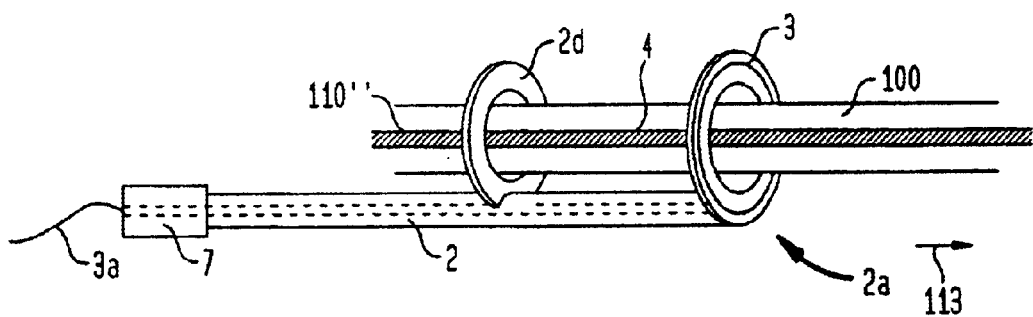
FIG. 4I is a sectional view of a sixth embodiment of a vein stripper according to the present invention, having a coagulation and cutting instrument with a displacement device, and a probe configured as electrode.
Figure 4J:
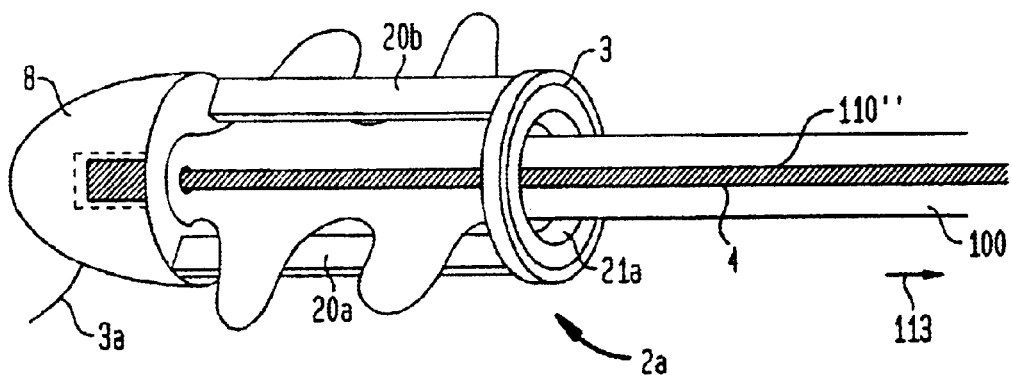
FIG. 4J is a sectional view of a seventh embodiment of a vein stripper according to the present invention, having a probe configured as electrode.
Figure 4K:
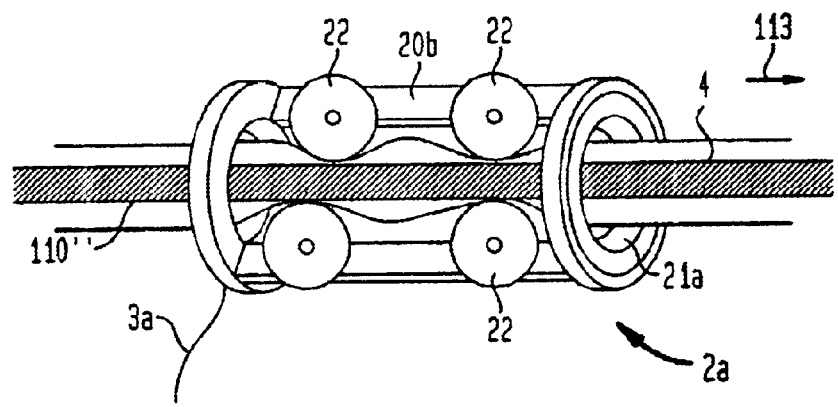
FIG. 4K is a sectional view of an eighth embodiment of a vein stripper according to the present invention, having a coagulation and cutting unit with a drive assembly and a probe configured as electrode.

FIGS. 4I to 4K show vein strippers according to the invention, each including a probe 110" which is designed to form the electrode 4 so that it is sufficient to provide only one electrode 3 at the coagulation and cutting device 1 to implement the cutting and coagulation operation. The substantially ring-shaped configuration of the electrode 3 of the coagulation and cutting instrument 1 ensures a cutting and coagulation in all directions. Of course, the effectiveness of the coagulation and cutting instrument 1 can be improved by providing additional electrodes.

In all embodiments in which the probe 110, 110', 110" are moved conjointly with the coagulation and cutting instrument 1 during stripping procedure, the probe 110, 110', 110" may also be connected in one piece with the coagulation and cutting instrument 1.

It has been shown that during application of the vein stripper, it is oftentimes necessary to briefly retract the vein stripper several times. This may be realized by pulling the electric lines 3a, 4a, connected to the electrodes 3, 4, or by pulling a cable, which surrounds the electric lines 3a, 4a, when the lines 3a, 4a or the cable are guided outwards from the end face 2b of the base body 2. In situations, where the cable is secured eccentrically on the base body 2, a tilting of the coagulation and cutting instrument 1 in the lumen may then be encountered. Therefore, as shown in the embodiment of FIGS. 5A to 5D, the electric lines 3a, 4a are guided outwards centrally from the end face 2b of the base body 2.

The coagulation and cutting instrument 17 shown in FIGS. 5A to 5D has in addition to the electrodes 3, 4 several further electrodes 5 provided in the area of the end face 2a of the base body 2 and substantially overlapping the electrodes 3, 4. The electrodes 5 define symmetry axes 5' in substantial parallel relationship to the symmetry axes 3', 4' of the other electrodes 3, 4. In axial direction of the symmetry axes 3', 4', 5', the areas covered by the electrodes 3, 4, 5 substantially overlap. The electrodes 5 may be attached to the outer wall surface 2c of the base body 2 or to the inner wall surface thereof. Of course, the attachment of further electrodes directly to the end face 2a of the base body 2 is also possible.

The provision of several concentric electrodes 3, 4, 5 results in the formation of further activation zones 6 in which severed venous side branches 101 can be additionally coagulated. This is particularly advantageous for stopping bleeding as the repeated coagulation of the already severed open end of a vein branch provides for a best possible stoppage of bleeding. This is oftentimes required in situations of very thick or also very thin or brittle vein branches which otherwise still encounter some bleeding. When providing the coagulation and cutting instrument 1 with additional electrodes 5 on the side surface 2c of the base body 2, the ends of the problematic venous side branches 101 are coagulated automatically repeatedly to thereby realize a complete stoppage of bleeding.

A certain potential can be applied via separate lines to the additional ring-shaped electrodes 5, or the additional ring-shaped electrodes 5 can be connected to the other electrodes 3, 4. The first case offers the option to separately adjust the difference in potential for all activation zones 6, whereas the second case allows all electrodes 3, 4, 5 to be supplied via both electric lines 3a, 4a. The electrodes 3, 4, 5 of the coagulation and cutting instrument 1 according to FIGS. 5A to 5D are all connected via the electric lines 3a, 4a and have alternately the polarities of the lines 3a and the line 4a.

Different changes in potential between the individual electrodes 3, 4, 5 may also be implemented by changing the spacing between the electrodes 3, 4, 5 and/or through connection of at least one of the electrodes 3, 4, 5 with a resistor or the like. Examples of resistors include ohmic resistor or reactive impedance.

The base body 2 is configured in the form of a single wide shaft 20a to thereby provide sufficient space for the fold formation of the vein wall.

In the area of the end face 2b, the base body 2 includes a slot 8a in the sidewall 2c and a pocket 8b. The pocket 8b is narrowed on the side confronting the end face 2b of the body 2 by a web 8c which serves as holding unit 8 for receiving and securement of the end 110a of probe 110. The illustrated holding unit 8, in which the pocket 8b is formed with a prolongation 8d on the side confronting the end face 2b of the base body 2, enables a simple form-fitting connection between the base body 2 and the head-like end 110a of the probe 110. After placement of the probe 110 or its end 110a into the area of the slot 8a or the pocket 8b, the end 110a of the probe 110 can be fixed through retraction in pulling direction 113 in the prolongation 8d.

The provision of the holding unit 8 in the sidewall 2c allows a guidance of the electric lines 3a, 4a centrally outwards from the end face 2b. Thus, the coagulation and cutting instrument 1 can be moved back and forth in the vein lumen in a simple manner via the electric lines 3a, 4a and the probe 110.

In particular, in case the electric lines 3a, 4a are guided within the probe 110', there is the option to attach an additional drainage tube 36 to the end face 2b (shown, e.g. in FIG. 4F). The drainage tube or redon tube 36 is normally inserted into the strip lumen after extraction of the vein 100 to absorb additional tissue liquid. The configuration of the coagulation and cutting instrument 1 with attached drainage tube 36 facilitates, on the one hand, the insertion of this tube because the drainage tube 36 is inserted automatically into the vein lumen after removal of the vein 100. On the other hand, in case the electric lines 3a, 4a are guided within the probe 110', and the base body 2 can no longer be pulled back by the electric lines 3a, 4a, the vein stripper according to the invention can now be moved back and forth in the vein lumen by the redon or drainage tube 36. Fixation of the drainage tube 36 may be realized in various manner, for example through welding or clamping. Preferred, however, is the provision of a separate holding unit 35 on the base body 2 to secure the drainage tube 36. This affords the option to perform surgery on one leg, to leave the drainage tube 36 in the vein lumen, to secure a further drainage tube 36 with the holding unit 35 upon the base body 2 and to repeat the surgery on the other leg. Other embodiments of a vein stripper according to the invention may guide the electric lines 3a, 4a within the drainage tube 36.

Figure 5E:
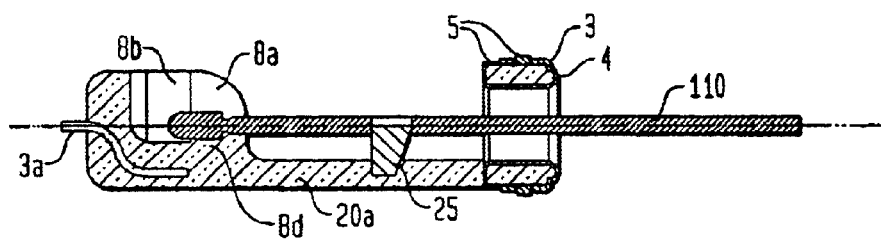
FIG. 5E is a sectional view of another variation of a coagulation and cutting unit with a longitudinal slitting structure.

FIG. 5E shows a sectional side view of a further embodiment of a coagulation and cutting instrument 1 which is provided with a longitudinal slitting structure 25 for slitting the vein 100 in longitudinal direction during stripping procedure and guiding the slitted region of the vein 100 about the end face 2b of the coagulation and cutting instrument 1. Thus, the coagulation and cutting instrument 1 can be pulled with the probe 110 through the strip lumen, whereby the vein 100 remains in the strip lumen and is extracted later from the strip lumen in a further operating step. During removal of the vein 100, a drainage tube may be inserted in the strip lumen. This procedure does not require the vein stripper according to the invention to receive the already stripped section of the vein 100 so that smaller structures of the vein stripper according to the invention are possible.

Longitudinal slitting of the vein 100 may be realized by a mechanical blade or by a slit electrode, whereby the slit electrode can cut bipolar or monopolar. When the slit electrode has a bipolar configuration, one of the other electrodes 5 may be used as counterelectrode. When the slit electrode is monopolar, the required power for cutting and coagulating the vein 100 and longitudinal slitting can be controlled independently from one another.

In the vein stripper according to FIG. 5E, the longitudinal slitting structure 25 is connected with the coagulation and cutting instrument 1, so that the slit electrode can be connected with one of the electric lines 3a, 4a. In particular, when a monopolar slit electrode is involved, the provision of a separate electric line has been proven beneficial.

Longitudinal slitting of the vein 100 is especially ensured, when the longitudinal slitting structure 25 is connected with the coagulation and cutting instrument 1 as well as with the probe 110, 110', 110". In this situation, the probe 110, 110', 110" is provided with a groove or the like for locked securement of the longitudinal slitting structure 25.

Figure 5F:
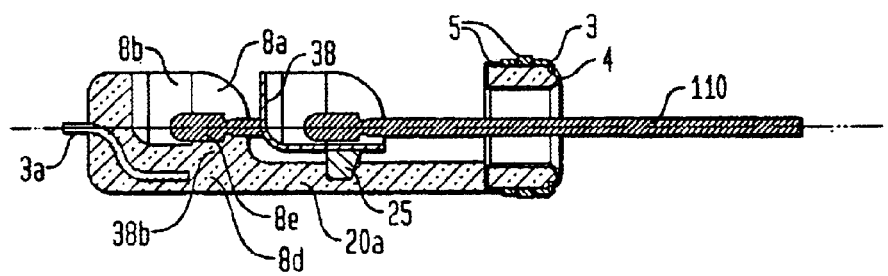
FIG. 5F is a sectional view of another variation of a coagulation and cutting instrument with a longitudinal slitting structure.
Figure 6A:
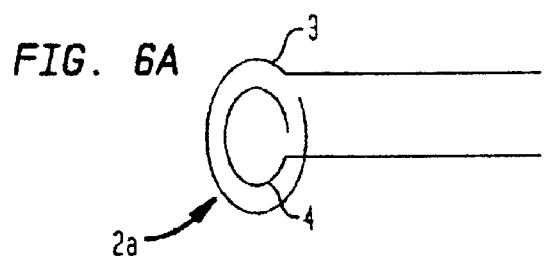
FIG. 6A is a schematic illustration of a first variation of an electrode assembly having electrodes formed with gaps.
Figure 6B:
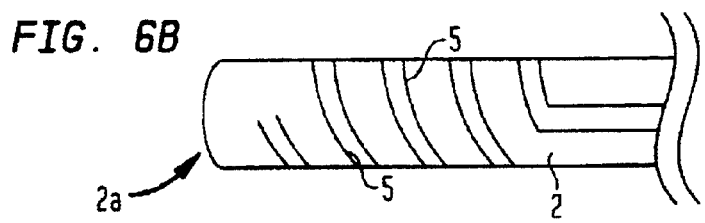
FIG. 6B is a schematic illustration of a second variation of an electrode assembly having helical electrodes.

According to another variation of a vein stripper according to the invention, shown in FIG. 5F, the longitudinal slitting structure 25 is connected to the holding unit 8 via a further holding unit 38 which is detachably mountable to the holding unit 8 via an engagement member 38a which hooks behind a shoulder of the holding unit 8e. The slitting structure 25 is connected in one piece to an underside of the holding unit 38 which is constructed to receiving and secure the end 110a, 110a', 110b' of the probe 110, 110', 110". In this embodiment, the longitudinal slitting structure 25 may be positioned between the probe 110, 110', 110" and the holding unit 8 of the coagulation and cutting instrument 1, thereby realizing a modular construction. Also this configuration of the longitudinal slitting structure 25 may be connected in one-piece with the coagulation and cutting instrument 1. As a result of the arrangement of the electrodes 3, 4, 5, the activation zone 6 extends in this embodiment essentially over the entire circumference of the base body 2. This characteristic can be attained also with a plurality of further electrode structures. For example, the electrodes 3, 4, 5 may be provided intermittently with gaps as shown in FIG. 6A. In this way, the electrodes 3, 4, 5 can be extended in a helical manner. FIG. 6B shows a coagulation and cutting instrument 1 in which two electrodes 5 are prolonged in helical manner over a longer portion of the base body 2, thereby realizing a greater activation zone 6.

Figure 6C:
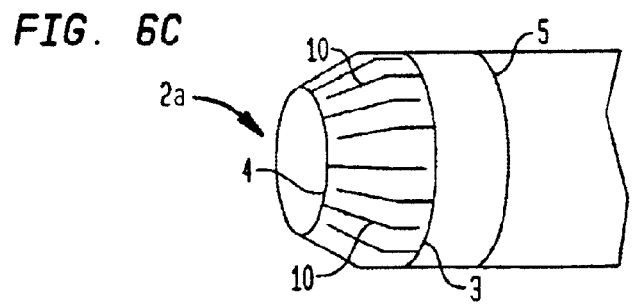
FIG. 6C is a schematic illustration of a third variation of an electrode assembly having electrodes with fan-like fingers.

In the embodiment of FIG. 6C, the electrodes 3, 4, 5 are formed with fan-like fingers 10. Also in this way, it is a possible to enlarge the activation zone 6.

Apart from stripping veins 100, the vein stripper according to the present invention can also be used for stripping other tubular tissue parts. For example, a portion of the esophagus may be stripped with the vein stripper according to the invention.

Figure 7:
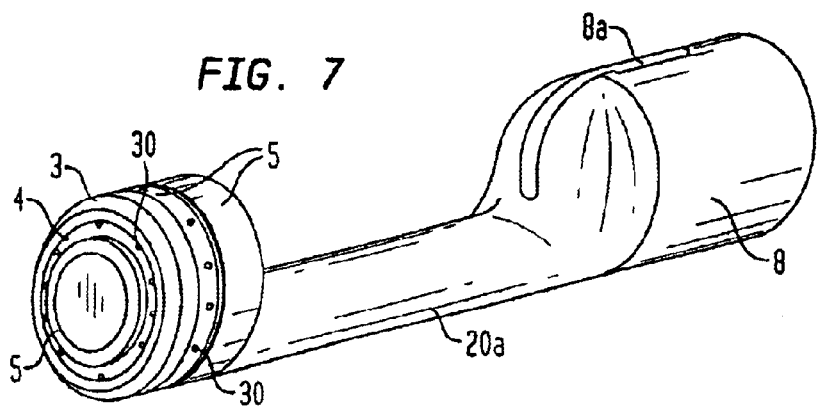
FIG. 7 is a perspective illustration of a tenth embodiment of a vein stripper according to the present invention with outlet openings.

Turning now to FIG. 7, there is shown another embodiment of a vein stripper according to the invention, which includes outlet openings 30 for an ionizable gas, e.g., argon. The outlet openings 30 are preferably arranged about the entire circumference of the vein stripper according to the invention, whereby it is possible to provide a plurality of outlet openings 30 or a single substantially ring-shaped outlet opening. Suitably, the electrodes 3, 4, 5 of same polarity are provided with the outlet openings 30, whereby the electrodes 3, 4, 5 of the other polarity are arranged adjacent to the electrodes 3, 4, 5 with the outlet openings 30.

The use of a vein stripper according to the invention without application of ionizable gas may cause coagulated crust of one of the side branches to adhere to the electrodes 3, 4, 5, whereby the crust may breakup during movement of the vein stripper and the side branch may start to bleed again. By pulling the vein stripper repeatedly through the vein, it is possible to realize a complete coagulation of the side branches without use of ionizable gas.

When used, ionizable gas exits through the outlet openings 30 and forms a gas cushion above the electrodes 3, 4, 5 with the outlet openings 30. When the gas cushion touches one of the electrodes 3, 4, 5 with different polarity, the gas ionizes and becomes conductive whereby the gas heats up and becomes plasma-like. Tissue touched by the gas cushion is coagulated by the gas in the absence of a direct contact of the tissue with one of the electrodes 3, 4, 5 so that adherence of crusts on the electrodes is prevented.

In order to ensure that the heat generated by the plasma-like ionized gas does not result in a coagulation directly on the electrodes 3, 4, 5, the electrodes 3, 4, 5 with the outlet openings 30 can be arranged offset to the neighboring electrodes 3, 4, 5 so that the formation of the gas cushion of plasma-like gas is realized above the electrodes 3, 4, 5 with the outlet openings 30. This gas cushion, which may be in particular ring-shaped, causes coagulation and prevents at the same time a direct contact of tissue to be coagulated with the electrodes 3, 4, 5.

When the gas cushion is in direct contact with only one of the electrodes 3, 4, 5, the contact to one of the electrodes 3, 4, 5 with another polarity may be realized also indirectly via the tissue. Hereby gas ionizes between the electrode 3, 4, 5 with the outlet openings 30 and the body tissue whereby gas heats up again and becomes plasma-like to coagulate the tissue. This situation is encountered especially when gas pressure is very low, the edges of the neighboring electrodes are contaminated, and/or much body liquid is experienced on the surfaces of the electrodes 3, 4, 5.

In the event, the electrodes 3, 4, 5 are arranged only slightly offset and the gas flow is interrupted, coagulation of tissue can be ensured through direct contact with the electrodes 3, 4, 5 to implement coagulation without assistance of ionizable gas.

Figure 8:
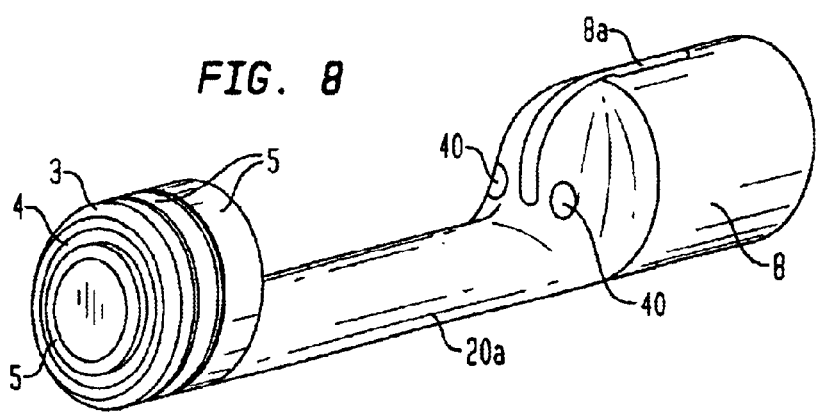
FIG. 8 is a perspective illustration of an eleventh embodiment of a vein stripper according to the present invention with suction openings.
Figure 9A:
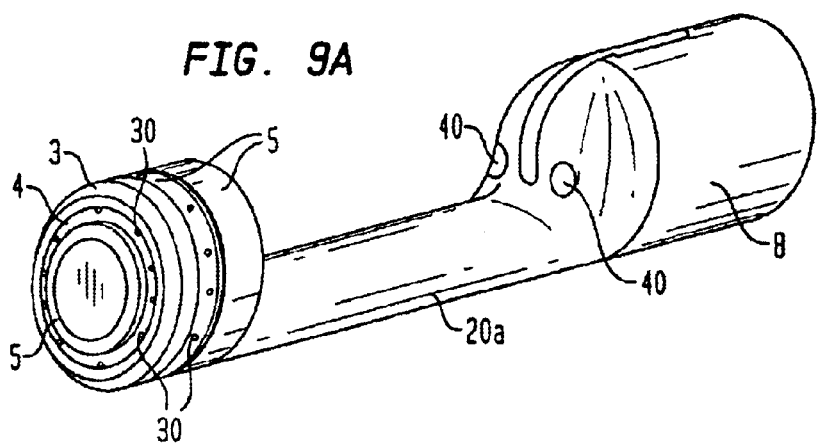
FIG. 9A is a perspective illustration of a twelfth embodiment of a vein stripper according to the present invention with outlet openings and suction openings.
Figure 9B:
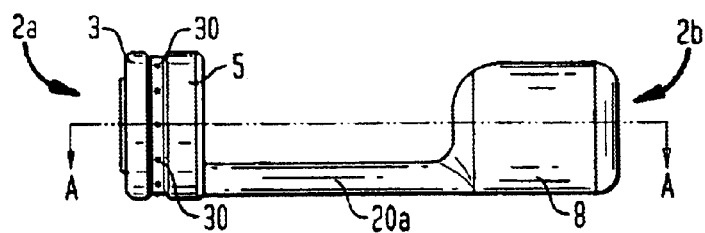
FIG. 9B is a side view of the vein stripper of FIG. 9A.
Figure 9C:
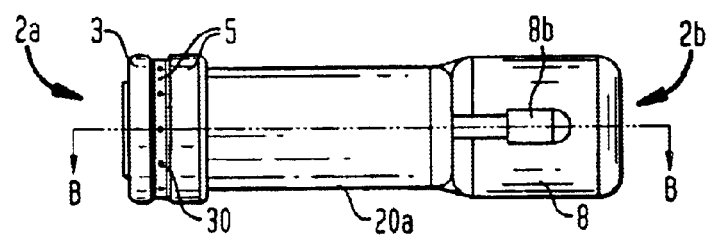
FIG. 9C is a top plan view of the vein stripper of FIG. 9A.
Figure 9D:
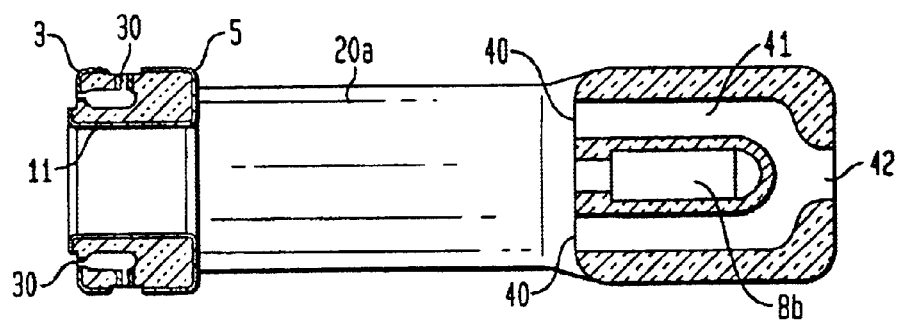
FIG. 9D is a sectional view of the vein stripper, taken along the line A—A in FIG. 9C.
Figure 9E:
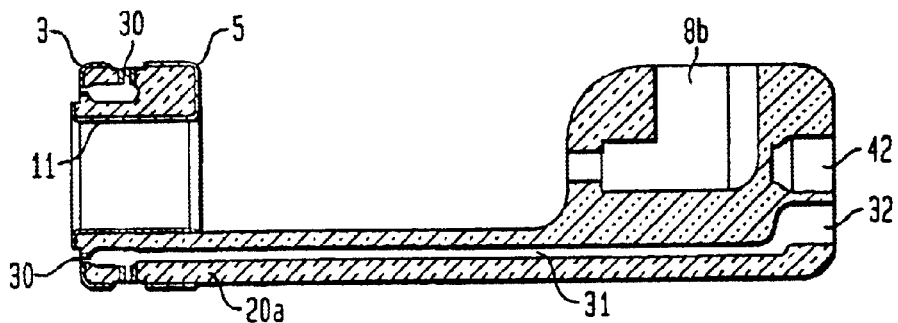
FIG. 9E is a sectional view of the vein stripper, taken along the line B—B in FIG. 9C.

FIG. 8 shows a vein stripper according to the invention with two suction openings 40 in the area of the holding unit 8 for sucking off smoke generated during coagulation. Of course, the number of suction openings 40 may vary. The arrangement of the suction openings 40 in the area of the holding unit 8 has the advantage that the electrodes 3, 4, 5 can be designed independently from the configuration of the suction openings 40. The provision of the suction openings 40 enables an immediate removal of generated smoke. It is also possible to provide the suction openings 40 in the shaft 20a. The holding unit 8 is provided with slot 8a for securement of the probe.

FIGS. 9A to 9E show another embodiment of a vein stripper according to the invention which includes outlet openings 30 as well as suction openings 40. As shown by the sectional views of FIGS. 9D and 9E, one of the electrodes 3, 4, 5 has a tubular portion 11. The tubular portion 11 exhibits a wide contact surface to thereby improve the conductive connection between the tubular portion 11 and the tissue. As further shown in FIGS. 9D and 9E, the outlet openings 30 are connected to a gas supply port 32 via a gas line 31. The gas supply port 32 may be arranged on the end face 2b of the base body 2, whereby the gas line 31 extends in parallel relationship to the electric lines 3a, 4a or a may be connected therewith. The suction openings 40 are connected via suction bores 41 with a suction port 42, which is, preferably, arranged also at the end face 2b of the base body 2. Thus, a suction line may also be guided in parallel relationship to the electric lines 3a, 4a or a may be connected therewith. The electric lines 3a, 4a, the gas line 31 and the suction line may also be fitted in a common tube.

Figure 10:
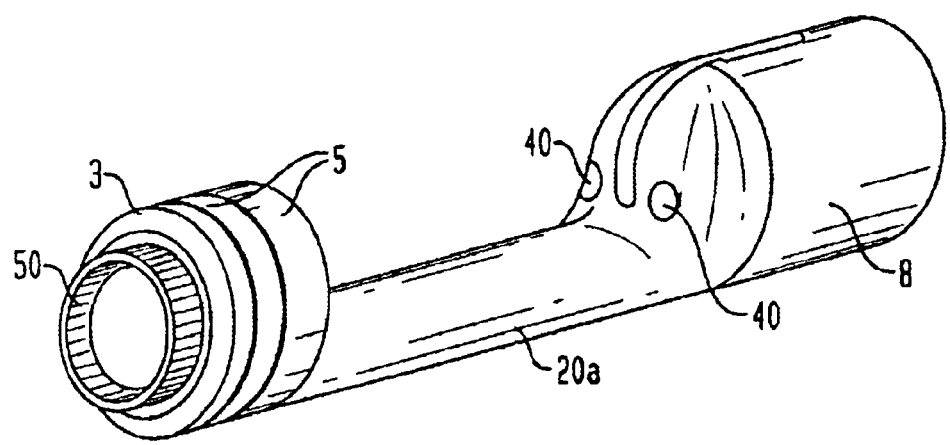
FIG. 10 is a perspective illustration of a thirteenth embodiment of a vein stripper according to the present invention with ultrasound resonator and suction openings.

FIG. 10 shows an embodiment of a vein stripper according to the invention which is provided in the area of the electrodes 3, 4, 5 with a ring-shaped ultrasonic resonator 50 which is configured as cutting instrument. The electrodes 3, 4, 5 form the coagulation device. In this embodiment, the cutting and coagulation steps are implemented differently so that both steps can be controlled separately in a simple manner.

The embodiments according to FIGS. 7 to 10 may, of course, also be provided with a longitudinal slipping structure 25. Further, the provision of an ultrasonic resonator 50 and/or the suction openings 40 and/or the outlet openings 30 may be provided in all embodiments.

While the invention has been illustrated and described as embodied in a vein stripper, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

What is claimed is:

1. A vein stripper for removing diseased veins, comprising:
   a probe insertable in a vein; and
   a coagulation and cutting instrument having an electrode assembly which includes at least two electrodes arranged at one end of the coagulation and cutting instrument to define a front opening for passage of the probe, wherein the probe with the vein is connected to the coagulation and cutting instrument at a predetermined location and surrounded in coaxial relationship by the electrode assembly.

2. The vein stripper of claim 1, wherein at least one of the electrodes is ring-shaped.

3. The vein stripper of claim 1, wherein at least one of the electrodes has a helical configuration.

4. The vein stripper of claim 1, wherein at least one of the electrodes has gaps.

5. The vein stripper of claim 1, wherein at least one of the electrodes includes fan-like fingers.

6. The vein stripper of claim 1, wherein the coagulation and cutting instrument includes a drive assembly so as to be self-propelled for movement along the vein.

7. The vein stripper of claim 1, wherein the electrode assembly includes a further electrode so as to have at least three electrodes.

8. The vein stripper of claim 7, wherein the electrodes are arranged on an outer wall surface of the coagulation and cutting instrument.

9. The vein stripper of claim 1, wherein the electrodes are spaced from one another at different distances.

10. The vein stripper of claim 1, and further comprising a resistor for connection to at least one of the electrodes.

11. The vein stripper of claim 1, wherein the coagulation and cutting instrument has a base body defining a longitudinal axis, said at least two electrodes of the coagulation and cutting instrument defining a symmetry axis in substantial parallel relationship to the longitudinal axis of the base body, wherein the electrodes define areas which substantially overlap in an axial direction of the symmetry axes.

12. The vein stripper of claim 11, wherein the base body bounds a substantially cylindrical space.

13. The vein stripper of claim 1, and further comprising electric lines provided for connecting the electrodes with an electric power supply source and fed within the probe for connection with two contacts on one end of the probe, wherein the coagulation and cutting instrument has two contacts which are conductively connected with the electrodes to thereby form an electrically conductive connection between the electrodes and the electric power supply source, when the probe is received and secured in the coagulation and cutting instrument.

14. The vein stripper of claim 1, and further comprising a longitudinal slitting structure for slitting a vein in longitudinal direction.

15. The vein stripper of claim 14, wherein the longitudinal slitting structure has one member selected from the group consisting of a slitting electrode for monopolar cutting, a slitting electrode for bipolar cutting, and a mechanical blade.

16. The vein stripper of claim 14, and further comprising electric lines for connecting the electrodes with an electric power supply source, wherein the longitudinal slitting structure is connected to the coagulation and cutting instrument and includes a slitting electrode connected to the electric lines or a further electric line.

17. The vein stripper of claim 1, wherein the coagulation and cutting instrument is provided in an area between the electrodes with at least one outlet opening for exit of an ionizable gas.

18. The vein stripper of claim 17, wherein the gas is argon.

19. The vein stripper of claim 17, wherein the coagulation and cutting instrument has a base body defining a longitudinal axis and having a forward end for arrangement of the at least two electrodes, wherein the outlet opening is connected to a gas supply port at a rear end of the base body.

20. The vein stripper of claim 1, wherein the coagulation and cutting instrument has at least one suction opening for removal of smoke.

21. The vein stripper of claim 1, and further comprising a ring-shaped ultrasonic resonator arranged in the area of the electrodes in immediate proximity around the front opening.

22. The vein stripper of claim 1, wherein the probe is a guide wire.

23. The vein stripper of claim 1, and further comprising an electric cable secured to the coagulating and cutting instrument to connect the electrodes to an electric power source.

24. The vein stripper of claim 1, wherein the predetermined location is a rear area of the coagulating and cutting instrument.

25. The vein stripper of claim 24, wherein the coagulating and cutting instrument includes a slot in the rear area to define the predetermined location for securement of the probe.

* * * * *

UNITED STATES PATENT AND TRADEMARK OFFICE
CERTIFICATE OF CORRECTION

PATENT NO. : 6,858,027 B2
DATED : February 22, 2005
INVENTOR(S) : Redtenbacher et al.

It is certified that error appears in the above-identified patent and that said Letters Patent is hereby corrected as shown below:

<u>Title page,</u>
Item [12], should read -- Redtenbacher --.
Item [75], Inventor, should read -- Michael Redtenbacher, Vienna (AT) --.

Signed and Sealed this

Sixth Day of June, 2006

JON W. DUDAS
*Director of the United States Patent and Trademark Office*